US012778940B2

(12) United States Patent
Schramm et al.

(10) Patent No.: US 12,778,940 B2
(45) Date of Patent: Nov. 3, 2026

(54) AGENTS TO PREVENT TISSUE DAMAGE FROM *CLOSTRIDIUM DIFFICILE* INFECTIONS BY INHIBITION OF THE GUT-DAMAGING BACTERIAL TOXINS TcdA AND TcdB

(71) Applicants: ALBERT EINSTEIN COLLEGE OF MEDICINE, Bronx, NY (US); VICTORIA LINK LIMITED, Wellington (NZ)

(72) Inventors: Vern L. Schramm, New Rochelle, NY (US); Ashleigh S. Paparella, Bronx, NY (US); Peter Charles Tyler, Wellington (NZ)

(73) Assignees: ALBERT EINSTEIN COLLEGE OF MEDICINE, Bronx, NY (US); VICTORIA LINK LIMITED, Wellington (NZ)

( * ) Notice: Subject to any disclaimer, the term of this patent is extended or adjusted under 35 U.S.C. 154(b) by 582 days.

(21) Appl. No.: 17/997,889

(22) PCT Filed: May 6, 2021

(86) PCT No.: PCT/US2021/031072

§ 371 (c)(1),
(2) Date: Nov. 3, 2022

(87) PCT Pub. No.: WO2021/226330

PCT Pub. Date: Nov. 11, 2021

(65) Prior Publication Data

US 2023/0346760 A1 Nov. 2, 2023

Related U.S. Application Data

(60) Provisional application No. 63/043,495, filed on Jun. 24, 2020, provisional application No. 63/020,789, filed on May 6, 2020.

(51) Int. Cl.

| | |
|---|---|
| *A61K 31/445* | (2006.01) |
| *A61K 45/06* | (2006.01) |
| *A61P 31/04* | (2006.01) |

(52) U.S. Cl.

CPC ............ *A61K 31/445* (2013.01); *A61K 45/06* (2013.01); *A61P 31/04* (2018.01)

(58) Field of Classification Search

CPC ........ A61K 31/445; A61K 45/06; A61P 31/04
See application file for complete search history.

(56) References Cited

U.S. PATENT DOCUMENTS

| | | | | |
|---|---|---|---|---|
| 7,501,439 | B2 | 3/2009 | Mugrage et al. | |
| 8,487,110 | B2 | 7/2013 | Rybczynski et al. | |
| 9,481,700 | B2 | 11/2016 | Rybczynski et al. | |
| 9,492,473 | B2 * | 11/2016 | von Maltzahn .... | A61K 31/7048 |
| 2015/0291940 | A1 | 10/2015 | Lotvin et al. | |
| 2017/0246201 | A1 | 8/2017 | Von Maltzahn et al. | |
| 2019/0202873 | A1 | 7/2019 | Jansen et al. | |

FOREIGN PATENT DOCUMENTS

| | | | |
|---|---|---|---|
| WO | 2010029313 | A1 | 3/2010 |
| WO | 2020219874 | A1 | 10/2020 |
| WO | 2020247480 | A1 | 12/2020 |

OTHER PUBLICATIONS

PubChem [Internet]. Bethesda (MD): National Library of Medicine (US), National Center for Biotechnology Information; 2004—. PubChem Compound Summary for CID 447607, Afegostat; [cited May 21, 2025]. Available from: https://pubchem.ncbi.nlm.nih.gov/compound/Afegostat (Year: 2005).*

Natarajan M, Walk ST, Young VB, Aronoff DM. A clinical and epidemiological review of non-toxigenic Clostridium difficile. Anaerobe. Aug. 2013;22:1-5. doi: 10.1016/j.anaerobe.2013.05.005. Epub May 29, 2013. PMID: 23727391; PMCID: PMC3729612. (Year: 2013).*

Carter GP, Rood JI, Lyras D. The role of toxin A and toxin B in Clostridium difficile-associated disease: Past and present perspectives. Gut Microbes. Jan. 2010;1(1):58-64. doi: 10.4161/gmic.1.1.10768. PMID: 20664812; PMCID: PMC2906822. (Year: 2010).*

Jank T, Ziegler MO, Schulz GE, Aktories K. Inhibition of the glucosyltransferase activity of clostridial Rho/Ras-glucosylating toxins by castanospermine. FEBS Lett. Jun. 25, 2008;582(15):2277-82. doi: 10.1016/j.febslet.2008.05.025. Epub May 27, 2008. PMID: 18505687. (Year: 2008).*

Gunasekara S, Vrielink A, Stubbs KA. Preliminary studies into the inhibition of the cholesterol alpha-glucosyltransferase from Helicobacter pylori using azasugars. Carbohydr Res. May 7, 2010;345(7):960-4. doi: 10.1016/j.carres.2010.03.003. Epub Mar. 4, 2010. PMID: 20307874. (Year: 2010).*

International Search Report and Written Opinion issued on Aug. 12, 2021 for corresponding PCT Application No. PCT/US2021/031072.

Tina M. Jespersen et al., "Isofagomine, a Potent, New Giycosidase Inhibitor," Angew. Chem. Int. Ed. Engl., vol. 33, No. 17, 1994, pp. 1778-1779.

Huizhen Liu et al., "Synthesis and Chemistry of Noeuromycin and Isofagomine Analogues," Journal of Carbohydrate Chemistry, 23:4, DOI: 10.1081/CAR-200030070; 2004, pp. 223-238.

European Search Report issued on Apr. 11, 2024 for corresponding European Application No. 21799992.9.

Christiane Goedl et al.: "Structure-function relationships for Schizophyllum commune trehalose phosphorylase and their implications for the catalytic mechanism of family GT-4 glycosyltransferases", Biochemical Journal, vol. 397, No. 3, 2006, pp. 491-500 XP055350974.

Wright, W. G. et al.: "Inhibition of catalytic and glucan-binding activities of a streptococcal GTF forming insoluble glucans", Caries Research, S. Karger AG, Basel, CH, vol. 36, No. 5, 2002, pp. 353-359 XP009108144.

(Continued)

*Primary Examiner* — Svetlana M Ivanova
(74) *Attorney, Agent, or Firm* — POLSINELLI PC

(57) ABSTRACT

Methods for treating or preventing diseases and conditions associated with *Clostridium difficile* infection are provided. The methods effectively inhibit bacterial pathogens induced UDP-glucose hydrolysis activity with minimized damage to host tissue.

19 Claims, 2 Drawing Sheets

(56) References Cited

OTHER PUBLICATIONS

Nidetzky, Bernd et al.: "[alpha]-Retaining glucosyl transfer catalysed by trehalose phosphorylase from Schizophyllum commune: mechanistic evidence obtained from steady-state kinetic studies with substrate analogues and inhibitors", Biochemical Journal, vol. 360, No. 3, 2001, pp. 727-736 XP093139376.
Steet, Richard et al.: "Selective action of the iminosugar isofagomine, a pharmacological chaperone for mutant forms of acid-[beta]-glucosidase", Biochemical Pharmacology, vol. 73, No. 9, 2007, pp. 1376-1383 XP029293295.
Thomas Jank et al.: "Inhibition of the glucosyltransferase activity of clostridial Rho/Ras-glucosylating toxins by castanospermine" , FEBS Letters, Elsevier, Amsterdam, NL, vol. 582, No. 15, 2008, pp. 2277-2282 XP071249378.
C. Darkoh et al.: "Harnessing the Glucosyltransferase Activities of Clostridium difficile for Functional Studies of Toxins A and B", Journal of Clinical Microbiology, vol. 49, No. 8, 2011, pp. 2933-2941 XP055138927.
Paparella, Ashleigh S. et al.: "Inhibition of Clostridium difficile TcdA and TcdB toxins with transition state analogues", Nature Communications, vol. 12, No. 1, 2021, pp. 1-13 XP093139173.
Paparella, Ashleigh S. et al.: "Isofagomine Inhibits Multiple TcdB Variants and Protects Mice from Clostridioides difficile-Induced Mortality", ACS Infectious Diseases, vol. 10, No. 3, 2024, pp. 928-937 XP093139406.
Pruitt, Rory N. et al.: "Structural Determinants of Clostridium difficile Toxin A Glucosyltransferase Activity", Journal of Biological Chemistry, vol. 287, No. 11, 2011, pp. 8013-8020 XP055871848.

* cited by examiner

TcdB Ki = 20.7 ± 3.3 uM

TcdA Ki = 15.0 ± 1.3 uM

TcdB Ki = 3.7 ± 0.3 uM
TcdA Ki = 1.8 ± 0.5 uM

TcdB (2x Ki UDP) = 1.5 uM
TcdA (2x Ki UDP) = 0.6 ± 0.1 uM

TcdB Ki = 21.0 ± 2.6 uM
TcdA Ki = 29.7 ± 3.7 uM

TcdB Ki = 17.9 ± 2.3uM
TcdA Ki = 5.2 ± 1.0 uM

Iminosugar Xylitol analogue
-No inhibition of TcdA and TcdB (200uM, 20uM, 2uM)
-No inhibition of TcdA and TcdB in presence of UDP

Isofagomine
Ki TcdB = 1.4 ± 0.1 μM
Ki TcdA = 0.24 ± 0.01 μM

AGENTS TO PREVENT TISSUE DAMAGE FROM *CLOSTRIDIUM DIFFICILE* INFECTIONS BY INHIBITION OF THE GUT-DAMAGING BACTERIAL TOXINS TcdA AND TcdB

CROSS-REFERENCE TO RELATED APPLICATIONS

This application is a national stage application (under 35 U.S.C. § 371) of PCT/US2021/031072, filed May 6, 2021, which claims the benefit of U.S. Provisional Patent Application No. 63/020,789 filed on May 6, 2020, and 63/043,495 filed on Jun. 24, 2020, the contents of which are hereby incorporated by reference herein.

STATEMENT REGARDING FEDERALLY SPONSORED R&D

This claimed invention was made with government support under Grant No. GM041916 awarded by the National Institute of Health. The government has certain rights in the invention.

TECHNICAL FIELD

Disclosed herein is a novel approach to the treatment and prevention of diseases and conditions associated with *Clostridium difficile* infection.

BACKGROUND

*Clostridium difficile* (*C. difficile*) infection is a serious disease caused by colon infection with *C. difficile* bacteria in humans. The infection is primarily caused by: (i) the disruption of the gut microbiome by the broad-spectrum antibiotic therapy; and (ii) the failure to produce neutralizing anti-toxin antibodies in patients. *C. difficile* bacteria produces two main toxins (namely, toxin A and toxin B), which glucosylate GTPases inside the epithelial cells, and lead to fever, abdominal pain, diarrhea, and colon inflammation.

TcdA and TcdB are 308 kDa and 270 kDa, respectively, multi-domain protein toxins sharing 49% sequence identity. TcdA and TcdB bind to target cells via a C-terminal receptor binding domain, triggering internalization by clathrin-mediated endocytosis. Acidification of endosomes causes pH-dependent conformational changes, leading to the formation of a trans-membrane pore and subsequent delivery of the N-terminal auto-processing cysteine protease domain (CPD) and glucosyltransferase domains (GTD) into the cytosol. The CPD is allosterically activated by intracellular inositol hexakisphosphate, catalyzing the release of the GTD into the cytosol. There, GTD glucosylates and inactivates Rho GTPases, including Rac1 and Cdc42 at Thr35 and RhoA at Thr37 in the switch I effector region using UDP-glucose as the glucosyl donor. Inactivation of Rho GTPases by the Tcd toxins causes actin-depolymerization resulting in a loss of structural integrity of the cell and eventually cell death through caspase-3 and caspase-9 dependent pathways. Although both toxins exhibit the same mechanism of cellular toxicity, it has been shown that TcdB is more potent than TcdA in its ability to induce cell rounding and cell death. Multiple studies to investigate the virulence of $TcdA^+TcdB^-$, $TcdA^-TcdB^+$ and $TcdA^+TcdB^+$ strains of *C. difficile* demonstrated that a $TcdA^+TcdB^-$ strain was less virulent than both $TcdA^-TcdB^+$ and $TcdA^+TcdB^+$ strains. A study in a hamster model demonstrated that a $TcdA^+TcdB^-$ strain was almost as virulent as $TcdA^+TcdB^+$ and $TcdA^-TcdB^+$ strains. Despite differences in species sensitivity, the sum of these studies indicates that both TcdA and TcdB are major determinants of *C. difficile* pathogenesis.

Conventional treatment of diseases associated with bacterial infection focuses on the use of several different antibiotics. These antibiotics include: (i) vancomycin (FDA-approved in 1986); (ii) metronidazole (not FDA-approved but is used "off-label"); and (iii) fidaxomicin (FDA-approved in 2011), a more narrow-spectrum antibiotic in comparison to vancomycin or metronidazole. Recently, there are reports indicating the rise of new strains of *C. difficile* bacteria that exhibit an increased toxin production and antibiotic resistance. An alternative means to treat bacterial infection involves the use of anti-toxin antibodies. Active immunization using bacterial toxin as a vaccine is presently in clinical trials. There is a need for developing new approaches to treating or preventing bacteria associated diseases.

SUMMARY

This patent document discloses inhibitory activities of iminosugars against virulence factors produced by bacterial pathogens such as *C. difficile*. The therapeutic approach based on this discovery for treating diseases associated with bacterial pathogens is an attractive option to antibiotic regimen because the human microbiota is spared while damage to host tissue is minimized.

An aspect of this document provides a method of treating a subject having a disease or condition associated with *C. difficile*, comprising administering to the subject a therapeutically effective amount of an iminosugar of Formula I or a pharmaceutically acceptable salt thereof, which includes for example isofagomine, noeuromycin, or a combination thereof.

Formula I

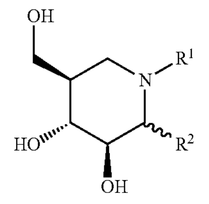

wherein $R^1$ is selected from the group consisting of H, a straight chain $C_{1-6}$ alkyl, a $C_{2-6}$ straight chain alkyl substituted with a hydroxyl, benzyl and phenyl;

$R^2$ is OH, or H;

represents a bond; and the carbon where $R^2$ is attached to has a R or S stereochemistry.

In some embodiments, the iminosugar is isofagomine or pharmaceutically acceptable salt thereof, wherein the isofagomine or pharmaceutically acceptable salt thereof inhibits the *C. difficile* toxins from interfering with the activities of Ras-related GTP-binding proteins. In some embodiments, the GTP-binding proteins are selected from the group consisting of Rho, Rac and Cdc42.

In some embodiments, the agent inhibits UDP-glucose hydrolysis and/or GTP-binding protein glucosyltransferase activity of a toxin released from the *C. difficile*. In some embodiments, the toxin is TcdA or TcdB.

In some embodiments, the disease is selected from gut inflammation, diarrhea, abnormal weight loss, colitis and toxic megacolon. In some embodiments, the subject is a human. In some embodiments, the method further comprises administering to the subject additionally an antibiotic.

In some embodiments, the compound is isofagomine which may be in the form of a tartrate salt. In some embodiments, the isofagomine is administered orally.

Another aspect of this document provides a method of preventing a *C. difficile* induced disease or condition in a subject, comprising administering to a subject exposed to *C. difficile* an effective amount of an iminosugar of Formula I, which includes for example isofagomine, noeuromycin, or a combination thereof. In some embodiments, the subject is exposed to or having a risk of being exposed to *C. difficile* and has not experienced any symptom of the disease of condition. In some embodiments, the method includes administering to the subject the compound of Formula I or the pharmaceutically acceptable salt thereof prior to any symptom of the disease or condition to prevent gastrointestinal damage.

In some embodiments, the *C. difficile* is a vegetative form of *C. difficile*, a *C. difficile* spore or a mixture of both.

In some embodiments, the compound is isofagomine, or pharmaceutically acceptable salt thereof which is capable of inhibiting UDP-glucose hydrolysis and/or GTP-binding protein glucosyltransferase activity of a toxin released from the *C. difficile*. In some embodiments, the toxin is TcdA or TcdB. In some embodiments, the subject is a human.

A further aspect provides a method of inhibiting UDP-glucose hydrolysis and/or GTP-binding protein glucosyltransferase activity induced by a toxin produced by bacteria, comprising contacting the toxin with an effective amount of an iminosugar of Formula I, which includes for example isofagomine, noeuromycin, or a combination thereof.

In some embodiments, the bacteria is *C. difficile*. In some embodiments, the toxin is TcdA or TcdB. The method further comprises contacting the bacteria with an antibiotic agent.

A further aspect provides a kit for treating a disease or condition associated with UDP-glucose hydrolysis and/or GTP-binding protein glucosyltransferase activity induced by a toxin produced by bacteria, comprising (a) a therapeutically effective amount of a compound of Formula I or a pharmaceutically acceptable salt thereof, which includes isofagomine, noeuromycin, or a combination thereof; and (b) an instruction for using the compound of Formula I or the pharmaceutically acceptable salt thereof for treating the disease or condition.

In some embodiments, the bacteria is *C. difficile*. In some embodiments, the toxin is TcdA or TcdB. In some embodiments, the kit further comprises an antibiotic agent.

DETAILED DESCRIPTIONS

Figure 1:
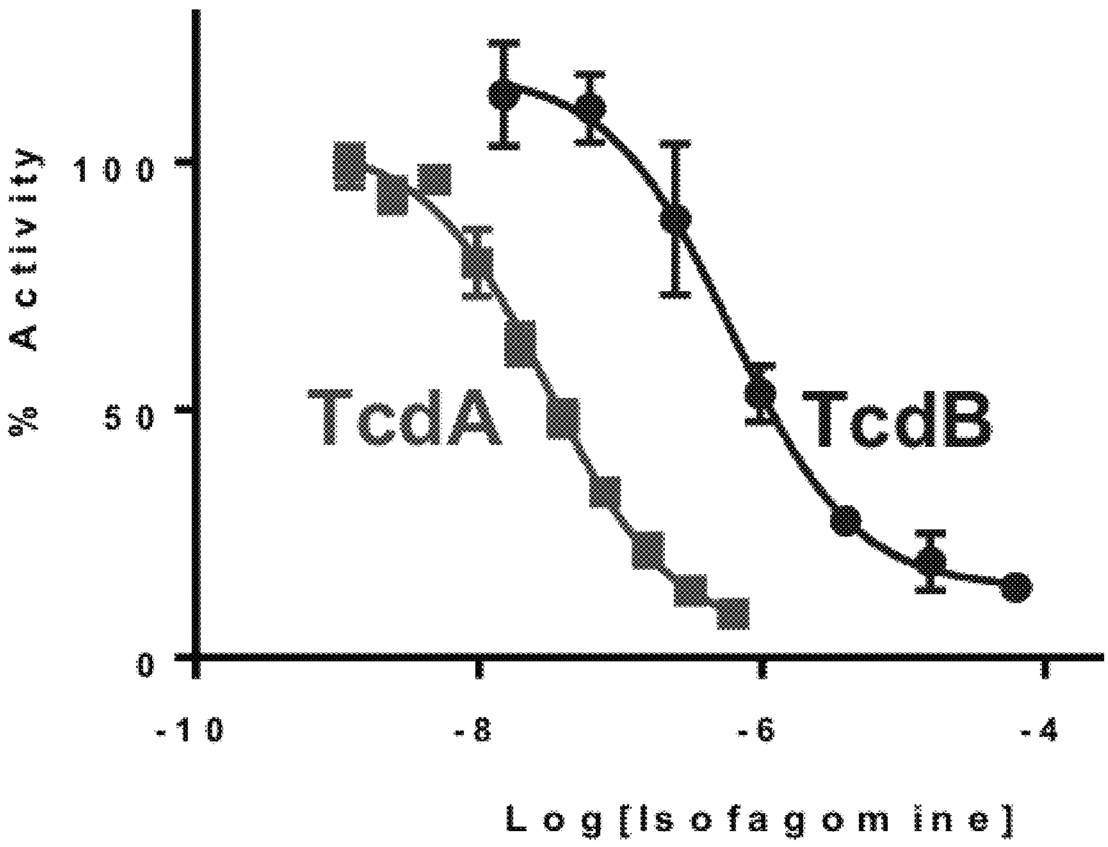
FIG. 1 shows inhibition of TcdB and TcdA by isofagomine, where glucosyltransferase reaction with UDP is at $2\times K_i$ value.

Various embodiments of this patent document discloses methods of treating or preventing bacteria-induced diseases. The methods are based on the inhibition by iminosugars such as isofagomine against hydrolysis activities of toxins released from the bacteria. In comparison with conventional methods, the methods disclosed herein selectively target a particular step of harmful events associated with the toxin. As a result, various diseases can be treated or prevented with minimum impact on beneficial gut bacteria in the host subject.

While the following text may reference or exemplify specific embodiments of a compound, a kit or a method relating to the treatment or prevention of a disease, it is not intended to limit the scope of the compound, kit or method to such particular reference or examples. Various modifications may be made by those skilled in the art, in view of practical and economic considerations, such as the specific salt form of the compound and the amount or frequency of administration of the therapeutic compound for treating or preventing a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term $C_{1-6}$ alkyl includes alkyl groups having 1, 2, 3, 4, 5, or 6 carbons. Non-limiting examples include methyl, ethyl, propyl, and butyl.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "subject" encompasses any animal, but preferably a mammal, e.g., human, non-human primate, a dog, a cat, a horse, a cow, or a rodent. More preferably, the subject is a human.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The term "pharmaceutically acceptable carrier" refers to a chemical compound that facilitates the delivery or incorporation of a compound or therapeutic agent into cells or tissues.

The term "pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4 -methylenebis(3-hydroxy- 2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "therapeutically effective amount" or "effective amount" refers to an amount of a compound or composition effective to prevent, alleviate or ameliorate symptoms of disease, prolong the survival of the subject being treated, or reach a desirable/acceptable medical or sanitary condition. Determination of a therapeutically effective amount or effective amount is well within the capability of those skilled in the art, especially in light of the detailed disclosure provided herein.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same.

The term "preventing" or "prevention" refers to a prophylactic treatment that is used to prevent progression of the disease or is used for precautionary purpose for persons at risk of developing the condition. The term includes action that occurs before a patient begins to suffer from *C. difficile* infection or associated disorder, such as but not limited to bowel or gastrointestinal disorder, that delays the onset of, and/or inhibits or reduces the severity of a *C. difficile* infection or *C. difficile* associated disease or symptom.

The methods of this patent document are based on the inhibition of hydrolysis and/or GTP-binding protein glucosyltransferase activities of toxins produced by bacteria. Different from conventional antibiotic treatment which often does not differentiate harmful bacteria from healthy microbiome, the methods disclosed herein provide a more targeted approach to reduce or prevent damages caused by bacterial toxins. For instance, as shown in the examples, isofagomine effectively inhibits the UDP-glucose hydrolysis and/or GTP-binding protein glucosyltransferase activity of TcdA and TcdB produced by *C. difficile* and protects cells from intoxication after challenge with either toxin. TcdA and TcdB cause cytotoxicity by glycosylating and inactivating Rho, Rac and Cdc cytoskeleton-stabilizing GTPases using UDP-glucose as the glucosyl donor. In the absence of GTPases, the toxins catalyze the slow hydrolysis of UDP-glucose. Studies show that the glycohydrolase reaction of the toxin involves the formation of a late, dissociative glucocation-like transition state where positive charge develops on the anomeric carbon. Without being bound by any particular theory, it is postulated that iminosugars of Formula I can mimic the glucocation transition state and inhibitive activities against the toxins.

Formula I

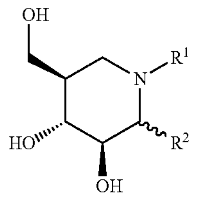

$R^1$ is selected from the group consisting of H, benzyl, phenyl, a straight chain or branched $C_{1-6}$ alkyl, and a $C_{2-6}$ straight chain or branched alkyl substituted with a hydroxyl;

$R^2$ is OH or H.

The aromatic ring of benzyl or the phenyl of $R^1$ is optionally substituted with one or more groups selected from straight chain or branched $C_{1-6}$ alkyl, halogen (F, Cl, Br, or I), $CF_3$, $OCF_3$, and $N(R^a)_2$, wherein each $R^a$ is independently a hydrogen or $C_{1-6}$ alkyl.

In some embodiments, $R^1$ is $C_{2-6}$ straight chain substituted with a hydroxyl at ω position (terminus position of the alkyl away from the ring nitrogen).

In some embodiments, $R^2$ is H. In some embodiments, $R^2$ is OH. In some embodiments, the carbon to which $R^2$ is attached has an R or S configuration. In some embodiments, the compound is a mixture of diastereomers (mixture of isomers with R and S configuration respectively at the carbon to which $R^2$ is attached.

In some embodiments, the compound of Formula I is selected from

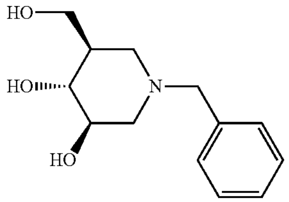
,
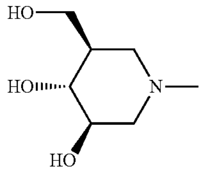
,
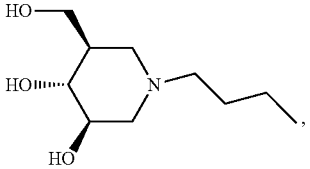
, and,
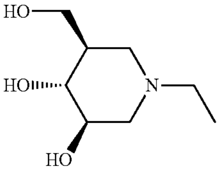
.

In some embodiments, the compound is isofagomine with the chemical name of (3R,4R,5R)-5-(hydroxymethyl)-3,4-piperidinediol having the following chemical structure:

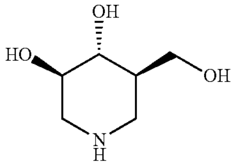

Synthesis of this compound is described in U.S. Pat. Nos. 5,844,102 to Sierks et al. and 5,863,903 to Lundgren et al. Isofagomine or noeuromycin can be combined with pharmaceutically acceptable salts, including for example salts of organic carboxylic acid salts such as acetic, lactic, tartaric, malic, isothionic, lactobionic, and succinic acids. In some embodiments, isofagomine is used in the form of a tartaric acid salt. Tartaric acid could have different stereoisomeric forms; D- or L-tartaric acid, or DL- or meso-tartaric acid. The term tartaric acid is intended to cover both D and L isomers as well as a DL mixture and meso-tartaric acid, and thus the term isofagomine tartrate is intended to include mono- or di-isofagomine-L-tartrate, mono- or di-isofagomine-D-tartrate, mono- or di-isofagomine-DL-tartrate and/or mono- or di-isofagomine-meso-tartrate. L-tartaric acid is (2R,3R)-(+)-tartaric acid with enantiomer enrichment of 97% or higher, and D-tartaric acid is (2S,3S)-(−)-tartaric acid with enantiomer enrichment of 97% or higher. DL-tartaric acid is a mixture of D- and L-tartaric acid with enantiomer enrichment of less than 97%.

Method of Treatment

Diseases or conditions associated with "*C. difficile*-associated disease" include any disease involving unwanted growth, toxin production, colonisation with *C. difficile* bacteria, cytotoxicity, gastrointestinal damage, histopathologic change in the gastrointestinal tract, gut inflammation, diarrhea, abnormal weight loss, colitis (e.g. pseudomembranous colitis), toxic megacolon, abdominal pain, fever, loss of appetite, cytotoxic megacolon, *C. difficile* colonisation, gastrointestinal damage, histopathologic change in the gastrointestinal tract, faecal shedding of *C. difficile* spores, and *C. difficile* associated mortality, and tissue invasion in the bowel by *C. difficile*. *C. difficile*-associated diseases or conditions are well known and specifically include antibiotic-associated diarrhea (also known as *C. difficile* colitis), pseudomembranous colitis, and *C. difficile*-associated toxic megacolon. *C. difficile* colitis generally refers to profuse, watery diarrheal illness associated with the presence of at least one *C. difficile* toxin. Pseudomembranous colitis refers to a severe form of *C. difficile* colitis further characterized by bloody diarrhoea, fever, and bowel wall invasion by *C. difficile*. The appearance of "pseudomembranes" on the surface of the colon or rectum may be diagnostic of the condition. The pseudomembranes are composed principally of inflammatory debris and white blood cells. *C. difficile*-associated diseases or condition also include a relapse of *C. difficile* infection in a subject who has suffered from *C. difficile* infection or *C. difficile*-associated disease previously.

A " strain" of *C. difficile* is a sample of *C. difficile* bacteria taken from an infected subject on a unique occasion. Routine methods may be used to distinguish between different *C. difficile* strains. Non-limiting examples of strains include KI, 630, R20291, M7404, VPI10463, CD196, R20291, 'CA', JGS6133, AI35, CD71, VPI10463, SP, CD37, CD84, CD39, M322832, JIR8078, M322630, CD63, FW07/06, and JIR8078.

An aspect of the patent document discloses a method of treating a subject having a disease or condition induced by or associated with *C. difficile*. The method includes administering to the subject a therapeutically effective amount of an iminosugar of Formula I or a pharmaceutically acceptable salt thereof. In some embodiments, the compound is isofagomine, noeuromycin, or a pharmaceutically acceptable salt thereof.

Various diseases or conditions can be induced by bacteria such as *Clostridium difficile* (*C. difficile*). Toxins including TcdA and TcdB catalyze glucosylation and the subsequent irreversible inactivation of target molecules. Isofagomine disrupts the toxin catalyzed glucosylation and helps maintains the normal functions of GTP-binding proteins including Rho, Rac and Cdc42. More specifically, isofagomine binds to the Tcd-UDP complex and inhibits the UDP-glucose hydrolysis and/or GTP-binding protein glucosyltransferase by serving as a mimic of the glucocation.

Diseases or conditions associated with bacteria such as *C. difficile* can be treated with the method disclosed herein. Non-limiting examples include diarrhea, abdominal pain, cramps, fever, inflammation on colonic biopsy, hypoalbuminemia, anasarca, abnormal weight loss, leukocytosis, sepsis, and/or asymptomatic carriage. In some embodiments, the disease is inflammation of gut epithelium. In some embodiments, the method further includes diagnosing a subject as having a disease or condition induced by *C. difficile* toxins.

The method is applicable to a human or an animal. The compound of Formula I or the pharmaceutically acceptable salt thereof can inhibit *C. difficile* from interfering with activities of Ras-related GTP-binding proteins selected from the group consisting of Rho, Rac and Cdc42. The compound or the pharmaceutically acceptable salt thereof can also inhibit UDP-glucose hydrolysis activity and/or GTP-binding protein glucosyltransferase activity of a toxin released from the *C. difficile*. In some embodiments, the method is used for the treatment of a human disease associated with *C. difficile*. In some embodiments, the toxin is TcdA or TcdB.

Various means of administration can be adopted under the direction of one of ordinary skill in the art. In some embodiments, the isofagomine or its pharmaceutically acceptable salt is administered orally to a subject.

In some embodiments of any method of this patent document, the compound is isofagomine or noeuromycin. Isofagomine or noeuromycin or the pharmaceutically acceptable salt thereof can be formulated in suitable forms including for example, a tablet, a capsule, a suspension, or a solution. In some embodiments, isofagomine is used in the form of a tartrate salt.

In some embodiments of any method of this patent document, the method further includes administering to the subject an antibiotic agent, sequentially or simultaneously. In some embodiments, the method excludes the administration of an additional antibiotic agent.

In some embodiments of any method of this patent document, there is included a step of administering uridine diphosphate glucose (UDP). UDP can be administered prior to, simultaneously with, or after the administration of the compound of Formula I or a pharmaceutically acceptable salt thereof.

Also discloses in this patent document is the use of a therapeutically effective amount of an iminosugar of Formula I or a pharmaceutically acceptable salt thereof to treat a disease or condition induced by or associated with *C. difficile*. The disease or condition, the means of administration, the dosage form and formulation, and the additional agents are as described above. In some embodiments, the compound is isofagomine, noeuromycin, or a pharmaceutically acceptable salt thereof.

This patent document further provides a therapeutically effective amount of an iminosugar of Formula I or a pharmaceutically acceptable salt thereof for use in the treatment of a disease or condition induced by or associated with *C. difficile*. The disease or condition, the means of administration, the dosage form and formulation, and the additional agents are as described above.

Method of Prevention

The compound of Formula I and pharmaceutically acceptable salts thereof can also be used for preventing the disease of condition associated with *C. difficile*, a relapse of a disease induced by *C. difficile*, or reducing frequency of the relapse or the reinfection in a subject. The method includes administering to the subject a therapeutically effective amount of an iminosugar of Formula I or a pharmaceutically acceptable salt thereof. In some embodiments, the subject may not have shown any symptom of a *C. difficile* associated disease or condition, and administration of the compound of Formula I and pharmaceutically acceptable salts thereof can serve a prophylactic role. When no symptom of a *C. difficile* associated disease or condition is observed, either the subject has not been infected with the bacteria or the bacteria has not caused any clinically determinable effect on the subject.

In some embodiments, the compound is isofagomine, noeuromycin, or a pharmaceutically acceptable salt thereof. The diseases to be prevented, the administration and the suitable form the active ingredient are similar to the method descried above and can be modified by one of ordinary skill in the art depending on the specific condition of the subject.

In some embodiments, the method includes administering to a subject exposed to or at risk of being exposed to *C. difficile* a therapeutically effective amount of an iminosugar of Formula I or a pharmaceutically acceptable salt thereof. A subject exposed to or at risk of being exposed to *C. difficile* may or may not have been infected, and if infected, may or may not have any symptom of *C. difficile* associated disease or condition. In some embodiments, the onset of the disease or condition has not taken place when iminosugar of Formula I or a pharmaceutically acceptable salt thereof is administered to the subject. In some embodiments, the compound is isofagomine, noeuromycin, or a pharmaceutically acceptable salt thereof. The *C. difficile* can be in any form including for example a vegetative form of *C. difficile*, a *C. difficile* spore or a mixture of both. As described above, isofagomine inhibits the UDP-glucose hydrolysis and/or GTP-binding protein glucosyltransferase activity of toxins such as TcdA and TcdB. In some embodiments, the subject is human.

Examples of subjects who are at risk of a *C. difficile* associated disease or condition include individuals at risk of or presently undergoing planned antimicrobial use; individuals at risk of or presently undergoing withdrawal of prescribed metronidazole or vancomycin; individuals who are at risk of or presently undergoing a planned admission to a healthcare facility (such as a hospital, chronic care facility, etc.) and healthcare workers; and/or individuals at risk of or presently undergoing a planned treatment with proton-pump inhibitors, H2 antagonists, and/or methotrexate, or a combination thereof individuals who have had or are undergoing gastrointestinal diseases, such as inflammatory bowel disease; individuals who have had or are undergoing gastrointestinal surgery or gastrointestinal procedures; and individuals who have had or are having a recurrence of a *C. difficile* infection and/or a CDAD, e.g., patients who have had a *C. difficile* infection and/or a CDAD once or more than once; individuals who are about 65 years old or older. Such at-risk subjects or patients may or may not be presently showing symptoms of a *C. difficile* infection.

Administration of an effective amount of the iminosugar (e.g. isofagomine, noeuromycin) or its pharmaceutically acceptable salt may, for example, prevent, decrease risk of, decrease severity of, decrease occurrences of, and/or delay outset of diarrhea; abdominal pain, cramps, fever, inflammation on colonic biopsy, hypoalbuminemia, anasarca, leukocytosis, sepsis, and/or asymptomatic carriage, etc., as compared to a subject to which the compound is not administered. In some embodiments, the presence of symptoms, signs, and/or risk factors of an infection is determined before beginning administration of isofagomine or noeuromycin.

In exemplary embodiments, isofagomine or noeuromycin, a solvate, or a pharmaceutically acceptable salt thereof is administered for at least 3, 4, 5, 6, or 7 days prior to an increased risk of acquiring *C. difficile* infection. In some embodiments, the compound is administered prior to admission to a hospital or a nursing home. In some embodiments, the compound is administered after admission to a hospital or a nursing home. In some embodiments, the method further includes administering to the subject an antibiotic agent.

Also discloses in this patent document is the use of a therapeutically effective amount of an iminosugar of Formula I or a pharmaceutically acceptable salt thereof for preventing a disease or condition associated with *C. difficile*, a relapse of a disease or condition associated with or induced by *C. difficile*, or reducing frequency of the relapse or the reinfection in a subject. The disease or condition, the means of administration, the dosage form and formulation, and the additional agents are as described above. In some embodiments, the compound is isofagomine, noeuromycin, or a pharmaceutically acceptable salt thereof.

This patent document further provides a therapeutically effective amount of an iminosugar of Formula I or a pharmaceutically acceptable salt thereof for use in preventing a disease or condition induced by or associated with *C. difficile*. The disease or condition, the means of administration, the dosage form and formulation, and the additional agents are as described above.

Method of Inhibition

Another aspect of the patent document provides a method of inhibiting UDP-glucose hydrolysis and/or GTP-binding protein glucosyltransferase activity induced by a toxin produced by bacteria. The method includes contacting the toxin with a therapeutically effective amount of a compound of Formula I or a pharmaceutically acceptable salt thereof. In some embodiments, the compound is isofagomine, noeuromycin, or a pharmaceutically acceptable salt thereof. In some embodiments, the contacting takes place in vivo. In some embodiments, the contacting takes place in a human or an animal. In some embodiments, the contacting takes place at in vitro condition. In some embodiments, the method further includes contacting the toxin or bacteria with a secondary agent such as an antibiotic agent.

In some embodiments, the UDP-glucose hydrolysis activity is associated with a disease selected from gut inflammation, diarrhea, weight loss, colitis, toxic megacolon, abdominal pain, fever, loss of appetite, cytotoxic megacolon, *C. difficile* colonisation, gastrointestinal damage, histopathologic change in the gastrointestinal tract, faecal shedding of *C. difficile* spores, and *C. difficile* associated mortality.

Isofagomine or noeuromycin may contact the toxin in any manner or under any suitable conditions to achieve the desirable inhibition. For instance, the compound after administration to a subject binds to the complex of Tcd (A or B) and UDP and therefore, directly or indirectly, contacts the toxin. Under in vitro conditions, isofagomine can similarly interact with the toxin through binding to the Tcd-UDP complex.

In some embodiments, the bacteria is *C. difficile*, which produces toxins including TcdA or TcdB. Through inhibition of the UDP-glucose hydrolysis activity, apoptosis induced by the toxins can be reduced. Various diseases associated with toxin modulated glucosylation and the subsequent irreversible inactivation of target molecules can thus be treated or prevented.

Also discloses in this patent document is the use of a therapeutically effective amount of an iminosugar of Formula I or a pharmaceutically acceptable salt thereof for inhibiting UDP-glucose hydrolysis and/or GTP-binding protein glucosyltransferase activity induced by a toxin produced by bacteria. The toxin, the bacteria, the disease or condition, the means of administration, the dosage form and formulation, and the additional agents are as described above. In some embodiments, the compound is isofagomine, noeuromycin, or a pharmaceutically acceptable salt thereof.

This patent document further provides a therapeutically effective amount of an iminosugar of Formula I or a pharmaceutically acceptable salt thereof for use in inhibiting UDP-glucose hydrolysis and/or GTP-binding protein glucosyltransferase activity induced by a toxin produced by bacteria. The toxin, the bacteria, the disease or condition, the means of administration, the dosage form and formulation, and the additional agents are as described above. In some embodiments, the compound is isofagomine, noeuromycin, or a pharmaceutically acceptable salt thereof.

Kit and Pharmaceutical Composition

Another aspect of the patent document provides a kit, which includes a compound of Formula I or a pharmaceutically acceptable salt thereof, or a pharmaceutical composition thereof and an instruction for treating or preventing diseases associated with C. difficile or inhibiting toxin modulated glucosylation. In some embodiments, the compound is isofagomine, noeuromycin, or a pharmaceutically acceptable salt thereof. In some embodiments, the kit further includes an antibiotic agent.

The pharmaceutical composition of the compound of Formula I, or a pharmaceutically acceptable salt thereof for the methods or kit describe above generally includes one or more pharmaceutically acceptable carriers. Nonlimiting examples of carriers include physiologically acceptable surface active agents, glidants, plasticizers, diluents, excipients, smoothing agents, suspension agents, film forming substances, and coating assistants. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents. Suitable exemplary binders include crystalline cellulose, sucrose, D-mannitol, dextrin, hydroxypropylcellulose, hydroxypropylmethylcellulose, polyvinylpyrrolidone, and the like. Suitable exemplary disintegrants include starch, carboxymethylcellulose, calcium carboxymethylcellulose, croscarmellose sodium, sodium carboxymethylstarch, and the like. Suitable exemplary solvents or dispersion media include water, alcohol (for example, ethanol), polyol (for example, glycerol, propylene glycol, and polyethylene glycol, sesame oil, corn oil, and the like), and suitable mixtures thereof that are physiologically compatible. Suitable exemplary solubilizing agents include polyethylene glycol, propylene glycol, D-mannitol, benzylbenzoate, ethanol, trisaminomethane, cholesterol, triethanolamine, sodium carbonate, sodium citrate, and the like. Suitable exemplary suspending agents include surfactants such as stearyltriethanolamine, sodium laurylsulfate, laurylaminopropionic acid, lecithin, benzalkonium chloride, benzethonium chloride, glycerin monostearate, coconut oil, olive oil, sesame oil, peanut oil, soya and the like; and hydrophilic polymers such as polyvinyl alcohol, polyvinylpyrrolidone, sodium carboxymethylcellulose, methylcellulose, hydroxy methylcellulose, hydroxy ethylcellulose, hydroxypropylcellulose, and the like. Suitable exemplary isotonic agent includes sodium chloride, glycerin, D-mannose, and the like. Suitable exemplary buffer agents include buffer solutions of salts, such as phosphate, acetates, carbonates, and citrates. Suitable exemplary soothing agents include benzyl alcohol, and the like. Suitable exemplary antiseptic substances include para-oxybenzoic acid esters, chlorobutanol, benzyl alcohol, phenethyl alcohol, dehydroacetic acid, sorbic acid, and the like. Suitable exemplary antioxidants include sulfite salts, ascorbic acid, and the like. Suitable exemplary sealers include, but are not limited to HPMC (or hypromellose), HPC, PEG and combinations thereof. Suitable exemplary lubricants include magnesium stearate, calcium stearate, talc, colloidal silica, hardened oil and the like.

In further exemplary embodiments for solid preparations, carriers or excipients include diluents, lubricants, binders, and disintegrants. In exemplary embodiments for liquid preparations, carriers include solvents, solubilizing agents, suspending agents, isotonic agents, buffer agents, soothing agents, and the like. Acceptable additional carriers or diluents for therapeutic use and the general procedures for the preparation of pharmaceutical compositions are well known in the pharmaceutical art, and are described, for example, in Remington's Pharmaceutical Sciences, 18th Ed., Mack Publishing Co., Easton, PA (1990), which is incorporated herein by reference in its entirety.

In any of the methods or kit disclosed herein, there may also include the administration of an additional antibiotic agent. The additional therapeutic agent functions in a synergistic or additive manner to enhance the therapeutic efficacy of isofagomine or noeuromycin in the treatment or prevention of *C. difficile* infection or a disease induced by *C. difficile* in a subject. Exemplary additional therapeutic agent includes, but not limited to, an antibiotic, antibody against the *C. difficile* (e.g., anti-toxins (TcdA or TcdB) or anti-endospores) and the like. In one example, the additional therapeutic agent is an antibiotic, e.g., vancomycin or metronidazole. In another example, the additional therapeutic agent is an antibody.

Additional therapeutic agent includes antibiotics that are used in the treatment of *C. difficile*. Such antibiotics may be used in combination with isofagomine or noeuromycin. Treatment of *C. difficile* infection by antibiotics relies on the ability of the antibiotics to kill off the *C. difficile* bacteria. Currently, there are at least three antibiotics commonly used in the clinics to treat *C. difficile* infection; namely, metronidazole, fidaxomicin and vancomycin. Metronidazole is marketed under the brand name "Flagyl®" and is a drug of choice for first episodes of mild-to-moderate *C. difficile* colitis. Several randomized controlled trials have demonstrated equivalent efficacy of oral metronidazole and oral vancomycin in treating the *C. difficile* colitis. (See, e.g., Zar, F. A. et al., "A comparison of vancomycin and metronidazole for the treatment of *C. difficile*-associated diarrhea" Clinical Infectious Diseases 45(3): 302-307, 2007) Fidaxomicin has the trade names "Dificid® or Dificlir®" (marketed under Cubist Pharmaceuticals) and it selectively eradicates the pathogenic *C. difficile* upon oral administration with minimal disruption of multiple species that made up the normal, healthy intestinal flora. Vancomycin has the trade name of "Vancocin®" and was first sold in 1954 and is available as a generic medication. Vancomycin is recommended by mouth as a treatment for severe *C. difficile* colitis.

Anti-*C. difficile* antibodies may encompass chimeric and humanized antibodies. These antibodies offer less antigenity upon administration into a human. Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (See, e.g., U.S. Pat. No. 4,816,567). Chimeric antibodies can also be created by recombinant DNA techniques where DNA encoding murine V regions can be ligated to DNA encoding the human constant regions. *C. difficile* antibodies include, for example, (i) antibodies that bind to a *C. difficile* toxin A; (ii) antibodies that bind to a *C. difficile* toxin B; (iii) antibodies that bind to both *C. difficile* toxin A and toxin B; (iv) antibodies that bind to a *C. difficile* vegetative cell antigen; and (v) antibodies that bind to a *C. difficile* endospore antigen. Exemplary anti-*C. difficile* toxin A antibodies include, for example, those disclosed in U.S. Pat. Nos. 8,236,311 and 8,986,697, U.S. 2013/0230531, WO 2014/144292, and W02013/028810. Exemplary anti-*C. difficile* toxin B antibodies include, for example, those disclosed in U.S. Pat. Nos. 8,236,311 and 8,986,697, U.S. 2013/0230531, WO 2014/144292, WO 2014/169344, and WO 2013/028810. Exemplary anti-*C. difficile* toxin A and toxin B antibodies include, for example, those disclosed in U.S. Pat. No. 8,236,311, U.S. 2013/0230531, and WO 2014/144292. Exemplary anti-*C. difficile* vegetative cell antigen or endospore antibodies include, for example, those disclosed in U.S. Pat. No. 8,697,374.

Administration Regimen

Isofagomine or noeuromycin, or a pharmaceutically acceptable salt thereof of a pharmaceutically composition thereof for the methods or kit described herein described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrastemally, or the like, including infusion pump delivery; as well as (d) administration topically; as deemed appropriate by those of skill in the art for bringing the active compound into contact with living tissue.

Advantageously, the pharmaceutical compositions of isofagomine or noeuromycin or a pharmaceutically acceptable salt thereof for administrations described above are prepared into dosage forms in a unit dose suited to fit a dose of the active ingredients. Such dosage forms in a unit dose include, for example, tablets, pills, capsules, injections (ampoules), suppositories, etc.

In exemplary embodiments of the pharmaceutical composition of isofagomine or noeuromycin or a pharmaceutically acceptable salt thereof for oral administration, the composition can be a tablet, coated tablet, capsule, caplet, cachet, lozenges, gel capsule, hard gelatin capsule, soft gelatin capsule, troche, dragee, dispersion, powder, granule, pill, liquid, an aqueous or non-aqueous liquid suspension, an oil-in-liquid or oil-in-water emulsion, including sustained release formulations that are known in the art. For pediatric and geriatric applications, suspensions, syrups and chewable tablets are especially suitable.

The therapeutically effective amount of isofagomine or noeuromycin, or a pharmaceutically acceptable salt thereof required as a dose will depend on the route of administration, the type of subject, including human, being treated, and the physical characteristics of the specific subject under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions can be chosen by the individual physician in view of the patient's condition. (see e.g., Fingl et al. 1975, in "The Pharmacological Basis of Therapeutics", which is hereby incorporated herein by reference in its entirety, with particular reference to Ch. 1, p. 1). In some embodiments, the dose range of isofagomine or noeuromycin, or a pharmaceutically acceptable salt thereof administered to the subject or patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively isofagomine or noeuromycin, or a pharmaceutically acceptable salt thereof may be administered by continuous intravenous infusion, preferably at a dose of up to about 1000 mg per day. As will be understood by those of skill in the art, in certain situations it may be necessary to administer isofagomine or noeuromycin, or a pharmaceutically acceptable salt thereof herein in amounts that exceed, or even far exceed, the above-stated, preferred dosage range in order to effectively and aggressively treat particularly aggressive diseases or infections. In some embodiments, the compound of Formula I or a pharmaceutically acceptable salt thereof (e.g. isofagomine or noeuromycin, or a pharmaceutically acceptable salt thereof) will be administered for a period of continuous therapy, for example for a week or more, or for months or years.

In some embodiments, the compound of Formula I or a pharmaceutically acceptable salt thereof is formulated into a dosage form for release for a period of 1 to 12, typically 3 to 12 hours, more typically 6-12 hours after administration. In some embodiments, the oral pharmaceutical compositions described herein may be administered in single or divided doses, from one to four times a day. The oral dosage forms may be conveniently presented in unit dosage forms and prepared by any methods well known in the art of pharmacy.

The compound of Formula I or a pharmaceutically acceptable salt thereof can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of isofagomine or noeuromycin, or a pharmaceutically acceptable salt thereof in humans.

The compound of Formula I or a pharmaceutically acceptable salt thereof may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising isofagomine or noeuromycin, or a pharmaceutically acceptable salt thereof formulated in a compatible pharmaceutical carrier may also be prepared, placed in an appropriate container, and labeled for treatment of an indicated condition.

Synthesis of Compounds of Formula I

The synthesis of compounds of Formula I can be readily accomplished from isofagomine or noeuromycin or stereoisomers thereof. As illustrated in Chart 1, through reductive amination reaction, the precursor containing NH reacts with a suitable aldehyde to provide Formula I. $R^{1a}$ is one carbon short from $R^1$ and the aldehyde carbon after reduction becomes the linking carbon to N. An exemplary reagent for the conversion is $NaBH_3CN$ in MeOH. Specific reaction condition and the amount of the reagents can be modified without undue experiments. Depending on the reactivity and nature of the precursor, a protecting group can be employed to prevent side reactions from happening. Additional examples for reductive amination and protection of functional groups include those in Bioorg. Med. Chem., 2001, 9, 733-744; Angew. Chem. Int. Ed., 2005, 44, 7450-7453; J. Med. Chem. 2007, 50, 94-100.

Chart 1

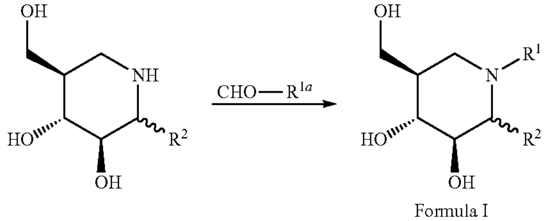

Formula I

All references cited herein are incorporated herein by reference in their entireties.

EXAMPLES

Example 1

Based on the accumulating ME evidence that both transition states for TcdB are glucocation-like, several iminosugar cations as chemical mimics of glucocations were analyzed (Chart 2). These include geometric features of the glucose hydroxyl groups and the proposed glucocation character by heterocyclic cationic nitrogens as shown below. A fully developed glucocation is planar (sp2) at C1 with the electron deficiency shared between C1 and the ring oxygen (O5). Gluconolactone shares the sp2 geometry at C1 but not the cation and is a poor inhibitor. Other iminosugars have similar hydroxyl group configurations to glucose, but with the ring oxygen or C1 replaced with an imino group to impart a potential cation at the ring oxygen or anomeric carbon position. Isofagomine is the best inhibitor for Tcds with a kinetic Ki of 290 nM for TcdB and 15 nM for TcdA in the presence of 2×Ki for UDP (FIG. 1). This and the uncompetitive pattern between isofagomine and UDP confirm inhibitor binding only to the Tcd-UDP complex, as expected from chemical considerations. Isofagomine chemical stability is endowed by its C2-deoxy. With a pKa value of 8.4, a fractional cation exists at physiological pH values. The contrasting poor inhibition by deoxynorjirimycin supports the importance of the cation charge at C1, the position for charge development in the TcdB transition state. Isofagomine binding supports catalytic site interactions with the 3, 4 and 6-hydroxyl groups together with the N1 cation. Noeuromycin Ki=4 μM for TcdB-UDP but 0.2 μM for TcdA-UDP, demonstrates clear differences for cation and hydroxyl group interactions for the Tcd isozymes.

Chart 2

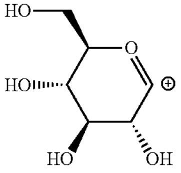

Glucocation

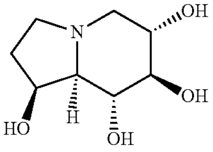

Castanospermine
0.68 ± 0.02 mM

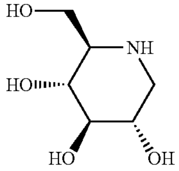

Deoxynojirimycin
> 10 mM

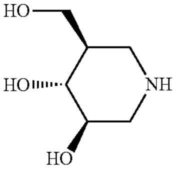

Isofagomine
0.29 ± 0.06 μM

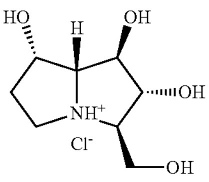

Australine•HCl
1.6 ± 0.4 mM

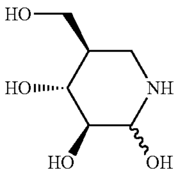

Noeuromycin
11 ± 1 μM

-continued

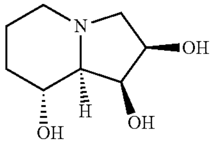

Swainsonine
> 10 mM

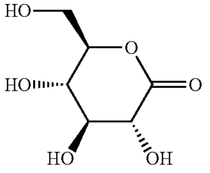

Gluconolactone
0.44 ± 0.03 mM

Mechanism of iminosugar inhibition: Isofagomine is uncompetitive with respect to UDP-glucose, indicating specific interaction with the TcdB-UDP product complex. When UDP is present at 2×Ki, the affinity of isofagomine increased 3-fold to give apparent Ki value of 290 nM for TcdB and tighter 15 nM for TcdA (preliminary result). ITC titration of TcdB showed no binding of isofagomine alone, and Kd=133 nM in the presence of excess UDP. The new data for TcdA-UDP-isofagomine predicts a Kd of 7 nM for isofagomine.

This is in the range of pharmaceutical efficacy and makes the prospect of tight binding inhibitors for the Tcd targets highly feasible. The result has consequences for the design of transition state analogs. In the most optimum case, linking two fragments that bind at the catalytic sites of target enzymes yields the product of the dissociation constants if optimal alignment can occur for both. For the UDP-isofagomine couple in TcdA the product of the dissociation constants are [11.5 μM×7 nM=81 fM]. For TcdB, the product of the dissociation constants are [11.5 μM×133 nM=1.5 pM]. The product of inhibitory fragment strengths can only be achieved when optimal interactions of both fragments are maintained at the catalytic site. Fragment alignment and optimal catalytic site interactions are best explored by structural analysis.

Structural analysis TcdB-inhibitor complexes: The catalytic domain of TcdB has now been co-crystallized with UDP, isofagomine and noeuromycin using sitting drop vapor diffusion (22° C.). Good quality crystals diffracted from 1.8 to 2.8 Å resolution (LRL-CAT beam line, Argonne, IL) at 0.97931 Å wavelength. Structures were solved by molecular replacement using PHASER and chain-A of TcdB (from PDB ID: SUQM) as the initial phasing model. Inhibitors and UDP were fitted into their electron densities with full occupancy. The geometry of bound UDP+isofagomine was compared with the structure of bound UDP-2F-glucose, a chemically stable analog reported previously for TcdB (SUQM). Isofagomine and the 2-F-glucose overlap closely. The cationic N1 of isofagomine forms a 2.7 Å ion pair to the β-phosphoryl oxygen of UDP, placing it in the same position as the covalently linked 2-F-glucose and with the same sugar ring pucker. The structural study supports the proposal that both UDP and isofagomine fragments are in near-optimal binding geometry. Noeuromycin occupies the same position as isofagomine.

Cell rounding studies were performed with CHO-K1 cells to test whether Isofagomine prevents TcdB induced cell rounding and cell death. Briefly, 50,000 CHO-K1 cells were seeded in 24-well plates and 100 μM Isofagomine was incubated with cells for 60 minutes. 100 pM full-length TcdB was added to cells and incubated for 24 hours. Cell Rounding was visualized by light microscopy. 100 μM Isofagomine was sufficient to protect CHO-K1 cells from rounding when treated with 100 pM TcdB.

Example 2

Isothermal Titration Calorimetry Experiments

Figure 2:
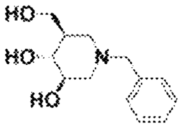
FIG. 2 shows results of exemplary compounds in inhibition assays.
Figure 2:
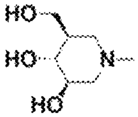
Figure 2:
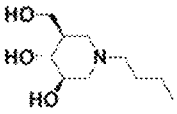
Figure 2:
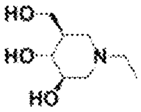
Figure 2:
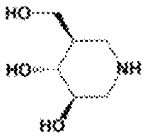

All ITC experiments were conducted on a Microcal PEAQ-ITC (Malvern Instruments). The experiments were performed at 25° C. in a cell containing 280 μL of reaction mixture (50 mM HEPES pH 7.5, 100 mM KCl, 4 mM $MgCl_2$, 1 mM $MnCl_2$) and 40 μM TcdB-GTD. The ligand was titrated into the protein solution over 19 injections of 2 μL of 6 s with a 150 s equilibration period between injections. For binding measurements involving UDP and isofagomine and noeuromycin, 40 μM TcdB-GTD was incubated with 1 mM UDP in the buffer described above for 30 min in the sample cell prior to titrating isofagomine or noeuromycin. The resulting data were fit to a model of one distinct binding site. The first injection for each sample was excluded from data fitting. Titrations were run past the point of enzyme saturation to correct for heats of dilution. Results of tested compounds are shown in FIG. 2.

Binding of Isofagomine in the presence of UDP—Quantitated by ITC $$K_D = 66.9 \pm 19.7\text{ nM}$$

$$\Delta H = -10.3 \pm 0.1\text{ kcal/mol}$$

$$\Delta G = -9.8 \pm 0.3\text{ kcal/mol}$$

$$-T\Delta S = .5 \pm 0.2\text{ kcal/mol}$$

$$N = 0.5 \pm 0.01$$

Binding of Noeuromycin in the presence of UDP—Quantitated by ITC $$K_D = 179.7 \pm 69.7\text{ nM}$$

$$\Delta H = -5.2 \pm 0.1\text{ kcal/mol}$$

$$\Delta G = -9.3 \pm 0.3\text{ kcal/mol}$$

$$-T\Delta S = 4.2 \pm 0.3\text{ kcal/mol}$$

$$N = 1.2 \pm 0.1$$

Example 3

Isofagomine and Noeuromycin Prevent TcdA- and TcdB-induced Cellular Toxicity

Isofagomine and noeuromycin were tested for the ability to prevent TcdA and TcdB induced toxicity. Cell rounding is a hallmark of TcdA and TcdB toxicity in mammalian cells and can be visualized by light microscopy. Isofagomine and noeuromycin were tested at 100 μM and were shown to prevent rounding of CHO-K1 cells induced by holotoxin TcdB (0.1 nM) or TcdA (0.5 nM). Similar results were observed with IMR90 and HT-29 cells. The mechanism of action for isofagomine and noeuromycin protection against Tcd toxins was determined by Western blot analysis of Rac1 glucosylation as described in literature. Rac1 glucosylation used anti-Rac1 antibody (Mab102) which distinguishes between un-glucosylated and glucosylated Rac1. IMR90 cells were treated with varying concentrations of isofagomine or noeuromycin (12.5 μM-100 μM) and TcdA (1 nM) or TcdB (0.1 nM). Treatment of IMR90 cells with increasing concentrations of either isofagomine or noeuromycin caused a dose-dependent maintenance of un-glucosylated Rac1 (Mab102) as compared to total Rac1 levels (anti-Rac1 23A8). Therefore, both iminosugars prevent toxin induced cell rounding through inhibition of TcdA and TcdB GT activity. Finally, we measured induction of apoptosis in the presence of TcdA and either isofagomine or noeuromycin, based on the protocol described in literature. Annexin V binds to phosphatidylserine which is exposed on the outer side of the cell membrane during early apoptosis. HT-29 cells were incubated with isofagomine or noeuromycin (250 μM or 500 μM) and analyzed for Annexin V signal by flow cytometry at 24 hr-post treatment. TcdA induced apoptosis, while addition of either iminosugar prevented apoptosis (FIGS. 4*c* and S11). Thus, isofagomine and noeuromycin prevent Tcd induced cell rounding of cultured mammalian cells via inhibition of Tcd GT activity and prevent apoptotic cell death in HT-29 cells. Isofagomine and noeuromycin are therefore attractive candidates for protection against TcdA and TcdB cellular toxicity in CDI.

Various procedures and animal models can be used to study the effect of the compounds disclosed herein. For instance, the methods disclosed in FEMS Microbiol. Lett 352(2014) 140-149; Am J Physiol Gastrointest Liver Physiol 312: G623-G627, 2017; US10046030 and US10144775 are suitable for studies in animal model. The entire disclosure of these references are hereby incorporated by references.

Tcd inhibitor animal toxicity and PK: Mice are given increasing concentrations of the test drugs (3-300 mg/kg) by oral gavage or i.p. administration for initial toxicity screening over a period of 5 days. Mice are observed following dosing for adverse response, including lethargy, loss of appetite, loss of motility, lack of grooming or dyspnea. Blood samples (5 μL, tail) are taken after administration of the test compounds. These provide samples for drug oral availability (i.p. vs oral comparison).

Safe doses (¼ and ⅛ observed toxicity) of orally available compounds are given by oral gavage to 2 groups of 3 mice (6 mice). Blood samples (5 μL, tail) are taken to analyze for PK by MS. Trials are for five days and 28 days for potential anti-toxins, with blood samples only on the first 4 days. At the end of the trial, animals are euthanized and their tissues examined by standard histology procedures to determine any harmful effect of the anti-toxins. Collection of urine and feces on day 4 permits analysis of anti-toxin excretion route and metabolism.

Protection against *C. diff.* infection by Tcd inhibitors. Mice are pretreated with oral antibiotics to disrupt the gut microbiome for 4 days, cleared of antibiotics for a day, and infected with $10^8$ *C. diff.* 630 (ATCC, expressing Tcd toxins only) on day one. Infections are untreated for 24 hr. Control infected groups remain untreated. Two treatment groups are given high (1× and 2×) but safe doses of drug once a day by i.p. or oral administration. Blood samples are taken once a day per mouse to follow drug and/or parasite levels where appropriate. After 5 days, treatment ceases and animals are compared to controls to determine if the infections or infective symptoms diminish. After two to three weeks, all animals are euthanized. Blood and tissue pathology samples are compared to controls for residual infection. Mice that become moribund because of infection are euthanized according to approved animal protocols.

Tcd transition state analog gut persistence: A driving rationale for the development of transition state analogs is their powerful persistence in biological systems, exemplified by single oral doses of DADMe-ImmH in humans. A similar effect against Tcds would prevent morbidity from *C. diff.* infections by small doses of prophylactic inhibitors. Note that the 0.5 mg/kg effective dose, is less than a single 50 mg dose for a 70 kg human, and is effective for multiple days. Here drug persistence in mice is tested.

Mice treated with varied single doses of transition state analogs are sacrificed at 6 hr intervals (n=3 per dose). The small and large intestines are flushed, segmented, frozen in liquid N2, extracted with methanol and analyzed by ms for transition state analog content. Internal mass standards of stable isotope-labeled inhibitors are added to the extraction tissue samples. Mass spectral analysis with internal standards establish the rate of cellular retention and/or cellular metabolism of the inhibitors.

Off-target analysis for mammalian glucosyltransferases: Humans express few O-glucosyltransferases, supporting the Tcd glucosyltransferases as focused targets. An exception is the Notch signaling pathway where O-glucosylation of specific serines is critical to the regulation of Notch function. In addition, transition state analogues of UDP-glucose could interfere with other steps of protein glycosylation or carbohydrate metabolism. In addition to the cell toxicity studies cultured cells treated with increasing concentrations of TcdB transition state analogs is analyzed for glycoprotein patterns by gel electrophoresis, followed by glycoprotein analysis.

It will be appreciated by persons skilled in the art that invention described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific component of a composition, or a step of the method, and may result from a different combination of described constituents, or that other un-described alternate embodiments may be available for a composition, kit or method, is not to be considered a disclaimer of those alternate embodiments. It will be appreciated that many of those un-described embodiments are within the literal scope of the following claims, and others are equivalent.

The invention claimed is:

1. A method of treating or preventing a disease or condition associated with *C. difficile*, comprising administering to a subject in need thereof a therapeutically effective amount of a compound of Formula I or a pharmaceutically acceptable salt thereof, wherein Formula I is represented as:

Formula I

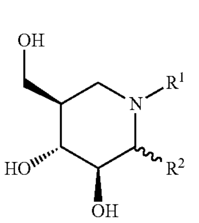

wherein, $R^1$ is selected from the group consisting of H, benzyl, phenyl, a straight chain $C_{1-6}$alkyl, and a $C_{2-6}$ straight chain alkyl substituted with a hydroxyl;

$R^2$ is OH, or H.

2. The method of claim 1, wherein $R^1$ is H and $R^2$ is H.

3. The method of claim 1, wherein the compound is isofagomine in the form of a tartrate salt.

4. The method of claim 1, wherein the compound is noeuromycin.

5. The method of claim 1, wherein the compound or the pharmaceutically acceptable salt thereof inhibits *C. difficile* from interfering with activities of Ras-related GTP-binding proteins selected from the group consisting of Rho, Rac and $Cdc_{42}$.

6. The method of claim 1, wherein the compound or the pharmaceutically acceptable salt thereof inhibits UDP-glucose hydrolysis activity and/or GTP-binding protein glucosyltransferase activity of a toxin released from the *C. difficile*.

7. The method of claim 6, wherein the toxin is TcdA or TcdB.

8. The method of claim 1, further comprising administering to the subject an antibiotic.

9. The method of claim 1, wherein the disease or condition is selected from gut inflammation, diarrhea, abnormal weight loss, colitis, toxic megacolon, abdominal pain, fever, loss of appetite, cytotoxic megacolon, *C. difficile* colonisation, gastrointestinal damage, histopathologic change in the gastrointestinal tract, faecal shedding of *C. difficile* spores, and *C. difficile* associated mortality.

10. The method of claim 1, wherein the subject is exposed to or having a risk of being exposed to *C. difficile* and has not experienced any symptom of the disease of condition.

11. The method of claim 1, comprising administering to the subject the compound of Formula I or the pharmaceutically acceptable salt thereof prior to any symptom of the disease or condition to prevent gastrointestinal damage.

12. The method of claim 1, comprising administering to the subject the compound of Formula I or the pharmaceutically acceptable salt thereof to prevent relapse of the disease or condition or reinfection of *C. difficile*, or reduce frequency of the relapse or the reinfection.

13. The method of claim 1, wherein the *C. difficile* is a vegetative form of *C. difficile*, a *C. difficile* spore or a mixture of both.

14. A method of inhibiting UDP-glucose hydrolysis activity and/or GTP-binding protein glucosyltransferase activity induced by a toxin produced by *C. difficile* bacteria, comprising contacting the toxin with an effective amount of a compound of Formula I or a pharmaceutically acceptable salt thereof.

15. The method of claim 14, wherein the toxin is TcdA or TcdB.

16. The method of claim 14, wherein the UDP-glucose hydrolysis activity is associated with a disease selected from the group consisting of gut inflammation, diarrhea, weight loss, colitis, toxic megacolon, abdominal pain, fever, loss of appetite, cytotoxic megacolon, *C. difficile* colonisation, gastrointestinal damage, histopathologic change in the gastrointestinal tract, faecal shedding of *C. difficile* spores, and *C. difficile* associated mortality.

17. The method of claim 14, wherein the compound is isofagomine or noeuromycin.

18. The method of claim 14, further comprising contacting the bacteria with an antibiotic agent.

19. A kit for treating a disease or condition associated with UDP-glucose hydrolysis activity and/or GTP-binding protein glucosyltransferase activity induced by a toxin produced by *C. difficile* bacteria, comprising:

(a) a therapeutically effective amount of a compound of Formula I or a pharmaceutically acceptable salt thereof; and (b) an instruction for using the compound of Formula I or the pharmaceutically acceptable salt thereof for treating the disease or condition.

* * * * *